United States Patent [19]
Mahurkar

[11] Patent Number: 5,836,921
[45] Date of Patent: *Nov. 17, 1998

[54] HYPODERMIC NEEDLE ASSEMBLY

[76] Inventor: Sakharam D. Mahurkar, 6171 N. Sheridan Rd., Suite 1112, Chicago, Ill. 60660

[ * ] Notice: The term of this patent shall not extend beyond the expiration date of Pat. No. 5,643,222.

[21] Appl. No.: 587,030

[22] Filed: Jan. 16, 1996

Related U.S. Application Data

[63] Continuation-in-part of Ser. No. 494,283, Jun. 23, 1995, Pat. No. 5,643,222, which is a continuation-in-part of Ser. No. 229,811, Apr. 19, 1994, Pat. No. 5,514,100, which is a division of Ser. No. 111,372, Aug. 23, 1993, Pat. No. 5,338,311.

[51] Int. Cl.$^6$ ........................................................ A61M 5/32
[52] U.S. Cl. ............................ 604/195; 604/198; 128/919
[58] Field of Search ..................... 604/195, 196, 604/110, 194, 198, 188, 240, 239, 242, 243, 197; 128/763–766, 919; 600/576–579

[56] References Cited

U.S. PATENT DOCUMENTS

| | | |
|---|---|---|
| D. 298,352 | 11/1988 | Raines . |
| 2,888,923 | 6/1959 | Cunha Reis . |
| 2,925,083 | 12/1960 | Craig . |
| 3,610,240 | 10/1971 | Harautuneian . |
| 3,658,061 | 4/1972 | Hall . |
| 4,068,659 | 1/1978 | Moorehead . |
| 4,233,982 | 11/1980 | Bauer et al. . |
| 4,245,635 | 1/1981 | Kontos . |
| 4,261,357 | 4/1981 | Kontos . |
| 4,274,408 | 6/1981 | Nimrod . |
| 4,417,886 | 11/1983 | Franhouser et al. . |
| 4,424,833 | 1/1984 | Spector et al. . |
| 4,425,120 | 1/1984 | Sampson et al. . |
| 4,468,224 | 8/1984 | Enzmann et al. . |
| 4,529,399 | 7/1985 | Groshong et al. . |
| 4,631,057 | 12/1986 | Mitchell . |

(List continued on next page.)

FOREIGN PATENT DOCUMENTS

| | | |
|---|---|---|
| 2004771 | 11/1969 | France . |
| 24 15 196 | 10/1975 | Germany . |
| 25 07 119 | 9/1976 | Germany . |
| 30 42 229 | 5/1982 | Germany . |

OTHER PUBLICATIONS

"Health Care" by Helene Cooper, Wall Street Journal (Nov. 25, 1992).
The G.M.P. Letter (May 1992).
Devices & Diagnostics Letter, vol. 19, No. 19 (May 8, 1992).
FDA Medical Bulletin, vol. 22, No. 2 (Sep. 22, 1992).
"Safer Syringes Boost Molder Opportunities" by Carl Kirkland, Plastic World, vol. 51/No. 8, pp. 20–24, (Aug. 1993).
"Ultrasonics Get Medical Seal of Approval" by Marcie Moskowitz, Plastic World, vol. 51/No. 8, pp. 26–28, (Aug. 1993).
Brochure for Arrow® Ravlerson Syringe.
Brochure for Syringes by Becton Dickinson of Franklin Lakes, New Jersey (1992).
Devices & Diagnostics Letter, p. 2 (Aug. 21, 1992).
Chiarello, Linda A., Reducing Needlestick Injuries among Health Care Workers: AIDS Clinical Care Oct. 1993 vol. 5 No. 10 Mass. Medical Society.

*Primary Examiner*—Ronald Stright, Jr.
*Attorney, Agent, or Firm*—Arnold, White & Durkee

[57] ABSTRACT

A needle-syringe assembly comprises an elongated, generally cylindrical barrel which forms a hollow nozzle located at the distal end of the barrel and which opens into the interior of the barrel. A plunger is slidably mounted in the barrel and forms a longitudinal cavity. A needle holder carries a hollow needle on the distal end, and the needle holder is slidably mounted in the longitudinal cavity of the plunger. The needle holder includes a lateral arm which extends between the plunger cavity and the barrel. A spiral channel or slot forms a guide surface which extends along a proximal end portion of the barrel for engaging the lateral arm of the needle holder and retracting the needle holder within the barrel in response to relative rotational movement between the barrel and the needle holder.

21 Claims, 10 Drawing Sheets

U.S. PATENT DOCUMENTS

| | | |
|---|---|---|
| 4,639,248 | 1/1987 | Schweblin . |
| 4,659,330 | 4/1987 | Nelson et al. . |
| 4,664,654 | 5/1987 | Strauss . |
| 4,666,435 | 5/1987 | Braginetz . |
| 4,693,708 | 9/1987 | Wanderer et al. . |
| 4,702,738 | 10/1987 | Spencer . |
| 4,710,170 | 12/1987 | Haber et al. . |
| 4,731,059 | 3/1988 | Wanderer et al. . |
| 4,731,068 | 3/1988 | Hesse . |
| 4,732,162 | 3/1988 | Martell . |
| 4,735,617 | 4/1988 | Nelson et al. . |
| 4,735,618 | 4/1988 | Hagen . |
| 4,742,910 | 5/1988 | Staebler . |
| 4,746,017 | 5/1988 | Howard et al. . |
| 4,747,831 | 5/1988 | Kulli . |
| 4,747,835 | 5/1988 | Sandhaus . |
| 4,747,836 | 5/1988 | Luther . |
| 4,752,290 | 6/1988 | Schramm . |
| 4,762,516 | 8/1988 | Luther et al. . |
| 4,767,412 | 8/1988 | Hymanson . |
| 4,767,413 | 8/1988 | Haber et al. . |
| 4,778,453 | 10/1988 | Lopez . |
| 4,782,841 | 11/1988 | Lopez . |
| 4,790,822 | 12/1988 | Haining . |
| 4,799,926 | 1/1989 | Haber . |
| 4,801,295 | 1/1989 | Spencer . |
| 4,808,169 | 2/1989 | Haber et al. . |
| 4,813,426 | 3/1989 | Haber et al. . |
| 4,813,938 | 3/1989 | Raulerson . |
| 4,816,024 | 3/1989 | Sitar et al. . |
| 4,819,659 | 4/1989 | Sitar . |
| 4,826,488 | 5/1989 | Nelson et al. . |
| 4,826,489 | 5/1989 | Haber et al. . |
| 4,826,491 | 5/1989 | Schramm . |
| 4,828,107 | 5/1989 | Spencer . |
| 4,828,548 | 5/1989 | Walter . |
| 4,832,696 | 5/1989 | Luther et al. . |
| 4,834,717 | 5/1989 | Haber et al. . |
| 4,838,871 | 6/1989 | Luther . |
| 4,842,591 | 6/1989 | Luther . |
| 4,846,811 | 7/1989 | Vanderhoof . |
| 4,850,961 | 7/1989 | Wanderer et al. . |
| 4,850,976 | 7/1989 | Heinrich et al. . |
| 4,852,584 | 8/1989 | Selby . |
| 4,863,435 | 9/1989 | Sturman et al. . |
| 4,863,436 | 9/1989 | Glick . |
| 4,869,717 | 9/1989 | Adair . |
| 4,872,552 | 10/1989 | Unger . |
| 4,874,383 | 10/1989 | McNaughton . |
| 4,874,384 | 10/1989 | Nunez . |
| 4,883,469 | 11/1989 | Glazier . |
| 4,887,998 | 12/1989 | Martin et al. . |
| 4,892,525 | 1/1990 | Hermann Jr. et al . . |
| 4,894,054 | 1/1990 | Miskinyar . |
| 4,894,055 | 1/1990 | Sudnak . |
| 4,897,083 | 1/1990 | Martell . |
| 4,898,588 | 2/1990 | Roberts . |
| 4,900,311 | 2/1990 | Stern et al. . |
| 4,903,832 | 2/1990 | Stewart . |
| 4,906,235 | 3/1990 | Roberts . |
| 4,909,794 | 3/1990 | Haber et al. . |
| 4,911,693 | 3/1990 | Paris . |
| 4,915,696 | 4/1990 | Feimer . |
| 4,915,697 | 4/1990 | DuPont . |
| 4,917,673 | 4/1990 | Coplin . |
| 4,919,656 | 4/1990 | Bracker et al. . |
| 4,921,489 | 5/1990 | Frizzell . |
| 4,927,019 | 5/1990 | Haber et al. . |
| 4,927,417 | 5/1990 | Moncada et al. . |
| 4,928,824 | 5/1990 | Barasch . |
| 4,929,241 | 5/1990 | Kulli . |
| 4,931,040 | 6/1990 | Haber et al. . |
| 4,931,048 | 6/1990 | Lopez . |
| 4,932,940 | 6/1990 | Walker et al. . |
| 4,932,946 | 6/1990 | Shields . |
| 4,935,013 | 6/1990 | Haber et al. . |
| 4,935,015 | 6/1990 | Hall . |
| 4,944,723 | 7/1990 | Haber et al. . |
| 4,944,728 | 7/1990 | Carrell et al. . |
| 4,944,731 | 7/1990 | Cole . |
| 4,946,447 | 8/1990 | Hardcastle et al. . |
| 4,950,241 | 8/1990 | Ranford . |
| 4,950,251 | 8/1990 | Haining . |
| 4,950,252 | 8/1990 | Luther et al. . |
| 4,958,622 | 9/1990 | Selenke . |
| 4,964,854 | 10/1990 | Luther . |
| 4,973,316 | 11/1990 | Dysarz . |
| 4,976,702 | 12/1990 | Andrews et al. . |
| 4,986,813 | 1/1991 | Blake, III et al. . |
| 4,986,819 | 1/1991 | Sobel . |
| 4,988,339 | 1/1991 | Vadher . |
| 4,994,034 | 2/1991 | Botich et al. . |
| 4,994,042 | 2/1991 | Vandher . |
| 4,994,044 | 2/1991 | LoDuca . |
| 4,997,422 | 3/1991 | Chow et al. . |
| 4,998,922 | 3/1991 | Kuracina et al. . |
| 5,000,167 | 3/1991 | Sunderland . |
| 5,002,536 | 3/1991 | Thompson et al. . |
| 5,013,304 | 5/1991 | Russell et al. . |
| 5,015,241 | 5/1991 | Feimer . |
| 5,019,045 | 5/1991 | Lee . |
| 5,019,051 | 5/1991 | Hake . |
| 5,024,326 | 6/1991 | Sandel et al. . |
| 5,024,660 | 6/1991 | McNaughton . |
| 5,026,345 | 6/1991 | Teringo . |
| 5,026,354 | 6/1991 | Kocses . |
| 5,030,209 | 7/1991 | Wanderer . |
| 5,030,212 | 7/1991 | Rose . |
| 5,037,400 | 8/1991 | Curry . |
| 5,037,401 | 8/1991 | DeCamp . |
| 5,045,062 | 9/1991 | Henson . |
| 5,046,508 | 9/1991 | Weissler . |
| 5,049,136 | 9/1991 | Johnson . |
| 5,051,109 | 9/1991 | Simon . |
| 5,053,017 | 10/1991 | Chamuel . |
| 5,057,088 | 10/1991 | Narayanan et al. . |
| 5,057,089 | 10/1991 | Greco . |
| 5,059,180 | 10/1991 | McLees . |
| 5,061,249 | 10/1991 | Campbell . |
| 5,066,279 | 11/1991 | Russell . |
| 5,066,281 | 11/1991 | Stevenson-Michener . |
| 5,067,942 | 11/1991 | Jaffe et al. . |
| 5,067,944 | 11/1991 | Nichols . |
| 5,067,946 | 11/1991 | Zhadanov . |
| 5,067,949 | 11/1991 | Freundlich et al. . |
| 5,069,669 | 12/1991 | Kole . |
| 5,078,693 | 1/1992 | Shine . |
| 5,084,019 | 1/1992 | Gartz . |
| 5,086,780 | 2/1992 | Schmitt . |
| 5,088,987 | 2/1992 | Noonan, Jr. . |
| 5,088,988 | 2/1992 | Talonn et al. . |
| 5,092,853 | 3/1992 | Couvertier, II . |
| 5,098,394 | 3/1992 | Luther . |
| 5,098,402 | 3/1992 | Davis . |
| 5,106,379 | 4/1992 | Leap . |
| 5,106,380 | 4/1992 | Lobello . |
| 5,108,378 | 4/1992 | Firth et al. . |
| 5,112,307 | 5/1992 | Haber et al. . |
| 5,112,315 | 5/1992 | Gloyer et al. . |
| 5,114,404 | 5/1992 | Paxton et al. . |
| 5,116,325 | 5/1992 | Paterson . |
| 5,120,309 | 6/1992 | Watts . |

| Patent No. | Date | Name |
|---|---|---|
| 5,122,118 | 6/1992 | Haber et al. . |
| 5,125,898 | 6/1992 | Kaufhold, Jr. et al. . |
| 5,127,910 | 7/1992 | Talonn et al. . |
| 5,135,504 | 8/1992 | McLees . |
| 5,135,505 | 8/1992 | Kaufman . |
| 5,147,324 | 9/1992 | Skakoon et al. . |
| 5,147,326 | 9/1992 | Talonn et al. . |
| 5,152,750 | 10/1992 | Haining . |
| 5,156,598 | 10/1992 | Skakoon et al. . |
| 5,160,326 | 11/1992 | Talonn et al. . |
| 5,163,908 | 11/1992 | Lambert . |
| 5,163,917 | 11/1992 | Huefner et al. . |
| 5,171,300 | 12/1992 | Blake III et al. . |
| 5,171,303 | 12/1992 | DeCamp . |
| 5,176,640 | 1/1993 | Nacci et al. . |
| 5,176,655 | 1/1993 | McCormick et al. . |
| 5,181,524 | 1/1993 | Wanderer et al. . |
| 5,183,468 | 2/1993 | McLees . |
| 5,188,119 | 2/1993 | Sunderland . |
| 5,188,611 | 2/1993 | Orgain . |
| 5,188,613 | 2/1993 | Shaw . |
| 5,190,526 | 3/1993 | Murray et al. . |
| 5,190,532 | 3/1993 | Yu . |
| 5,195,973 | 3/1993 | Novick . |
| 5,195,975 | 3/1993 | Castagna . |
| 5,195,982 | 3/1993 | Hoenig . |
| 5,195,983 | 3/1993 | Boese . |
| 5,195,992 | 3/1993 | Dudar et al. . |
| 5,195,993 | 3/1993 | Gianakos . |
| 5,197,953 | 3/1993 | Colonna . |
| 5,197,954 | 3/1993 | Cameron . |
| 5,201,718 | 4/1993 | Whisson . |
| 5,205,823 | 4/1993 | Zdeb . |
| 5,209,739 | 5/1993 | Talalay . |
| 5,211,629 | 5/1993 | Pressly et al. . |
| 5,215,524 | 6/1993 | Vallelunga et al. . |
| 5,215,525 | 6/1993 | Sturman . |
| 5,215,528 | 6/1993 | Purdy et al. . |
| 5,215,529 | 6/1993 | Fields et al. . |
| 5,215,533 | 6/1993 | Robb . |
| 5,215,534 | 6/1993 | DeHarde et al. . |
| 5,215,535 | 6/1993 | Gettig et al. . |
| 5,217,436 | 6/1993 | Farkas . |
| 5,217,437 | 6/1993 | Talonn et al. . |
| 5,219,333 | 6/1993 | Sagstetter et al. . |
| 5,219,338 | 6/1993 | Haworth . |
| 5,221,262 | 6/1993 | Kite . |
| 5,222,942 | 6/1993 | Bader . |
| 5,222,943 | 6/1993 | Mazzara . |
| 5,222,944 | 6/1993 | Harris . |
| 5,222,945 | 6/1993 | Basdnight . |
| 5,222,947 | 6/1993 | D'Amico . |
| 5,226,893 | 7/1993 | Kayser . |
| 5,232,456 | 8/1993 | Gonzalez . |
| 5,242,400 | 9/1993 | Blake, III et al. . |
| 5,246,428 | 9/1993 | Falknor . |
| 5,250,031 | 10/1993 | Kaplan et al. . |
| 5,254,099 | 10/1993 | Kuracina et al. . |
| 5,261,894 | 11/1993 | Smith et al. . |
| 5,267,961 | 12/1993 | Shaw . |
| 5,267,973 | 12/1993 | Haber et al. . |
| 5,267,976 | 12/1993 | Guerineau et al. . |
| 5,269,765 | 12/1993 | Kuracina . |
| 5,273,538 | 12/1993 | Chen . |
| 5,273,539 | 12/1993 | Chen . |
| 5,273,541 | 12/1993 | Malenchek . |
| 5,273,543 | 12/1993 | Bell et al. . |
| 5,279,582 | 1/1994 | Davison et al. . |
| 5,290,233 | 3/1994 | Campbell . |
| 5,295,975 | 3/1994 | Lockwood, Jr. . |
| 5,300,030 | 4/1994 | Crossman et al. . |
| 5,300,039 | 4/1994 | Poulsen . |
| 5,304,137 | 4/1994 | Fluke . |
| 5,304,149 | 4/1994 | Morigi . |
| 5,304,150 | 4/1994 | Duplan et al. . |
| 5,304,154 | 4/1994 | Gloyer et al. . |
| 5,312,347 | 5/1994 | Osborne et al. . |
| 5,312,365 | 5/1994 | Firth et al. . |
| 5,318,536 | 6/1994 | Williams . |
| 5,320,606 | 6/1994 | Jore . |
| 5,324,265 | 6/1994 | Murray et al. . |
| 5,336,186 | 8/1994 | Haber et al. . |
| 5,336,187 | 8/1994 | Terry et al. . |
| 5,336,197 | 8/1994 | Kuracina et al. . |
| 5,336,198 | 8/1994 | Silver et al. . |
| 5,338,304 | 8/1994 | Adams . |
| 5,342,323 | 8/1994 | Haining . |
| 5,344,403 | 9/1994 | Lee . |
| 5,352,208 | 10/1994 | Robinson . |
| 5,360,408 | 11/1994 | Vaillancourt . |
| 5,364,359 | 11/1994 | Van den Haak . |
| 5,376,080 | 12/1994 | Petrussa . |
| 5,378,240 | 1/1995 | Curie et al. . |
| 5,380,297 | 1/1995 | Wadman et al. . |
| 5,385,555 | 1/1995 | Hausser . |
| 5,393,301 | 2/1995 | Goldberg . |
| 5,395,337 | 3/1995 | Clemens et al. . |
| 5,399,170 | 3/1995 | Whitley . |
| 5,403,286 | 4/1995 | Lockwood, Jr. . |
| 5,403,431 | 4/1995 | Botich et al. . |
| 5,407,436 | 4/1995 | Toft et al. . |
| 5,415,645 | 5/1995 | Friend et al. . |
| 5,419,773 | 5/1995 | Rupp . |
| 5,643,222 | 7/1997 | Mahurkar ................................ 604/195 |

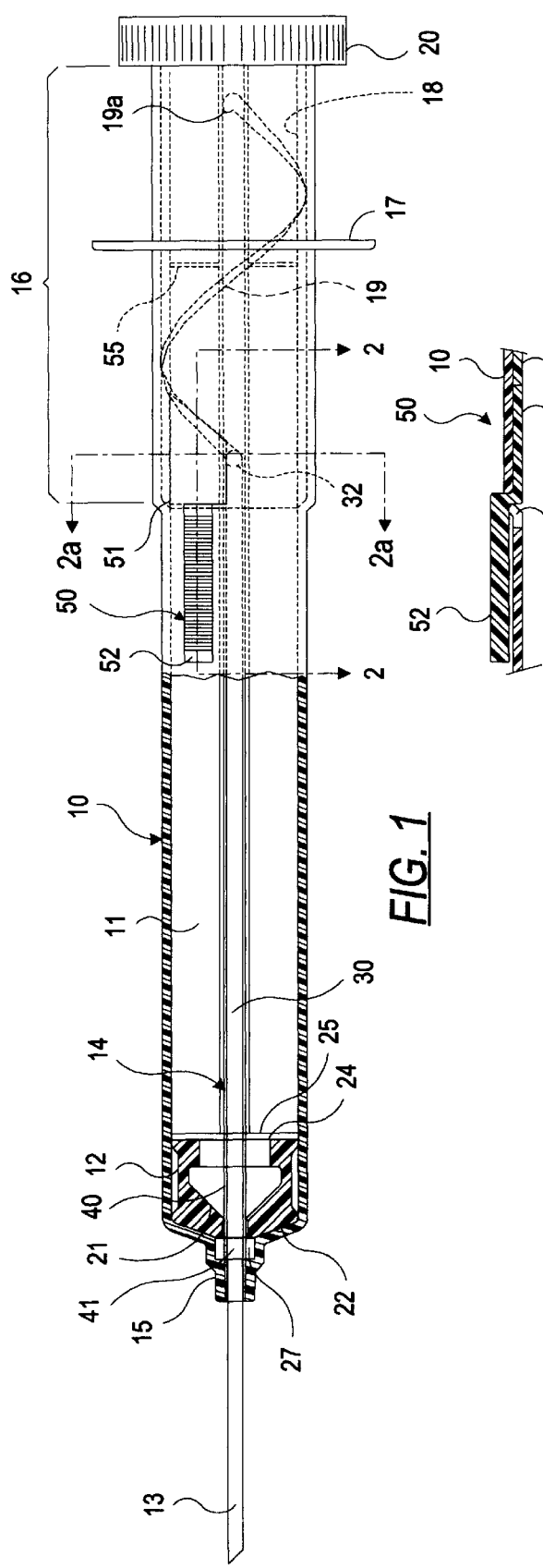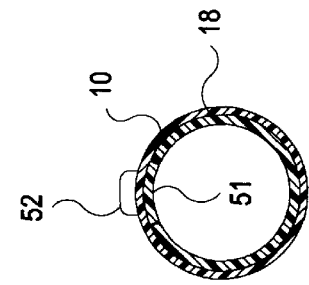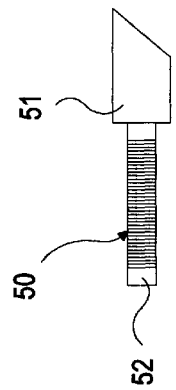

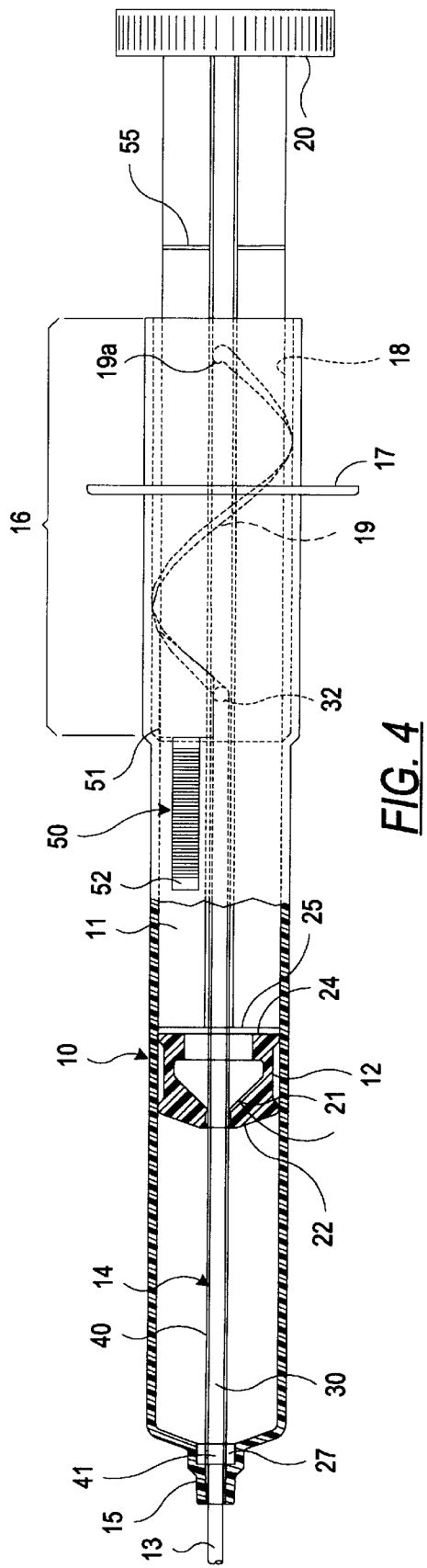
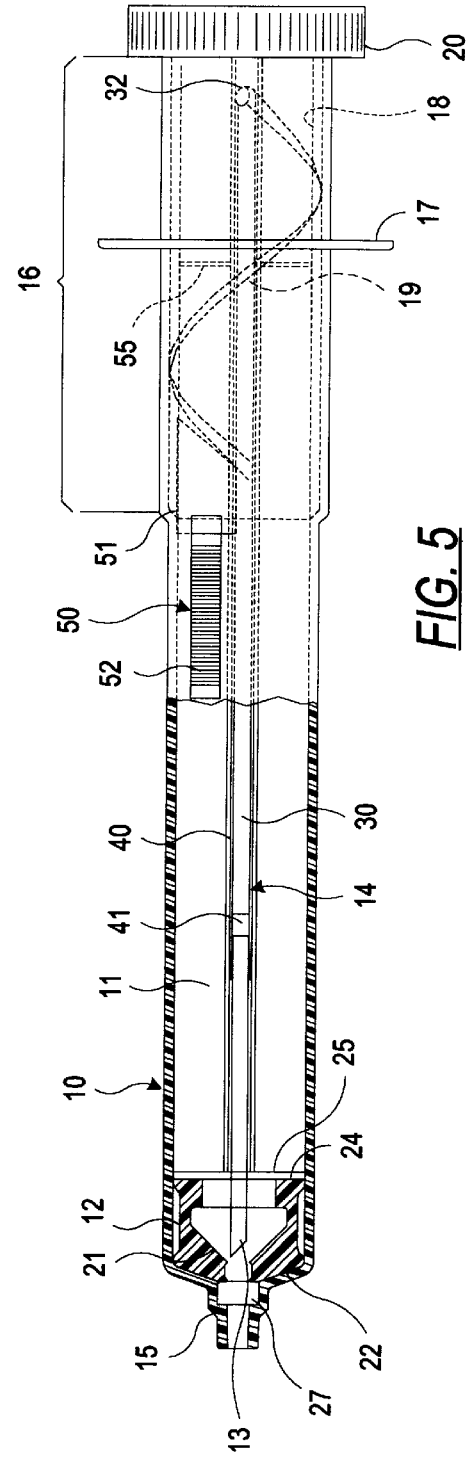
FIG. 4
FIG. 5

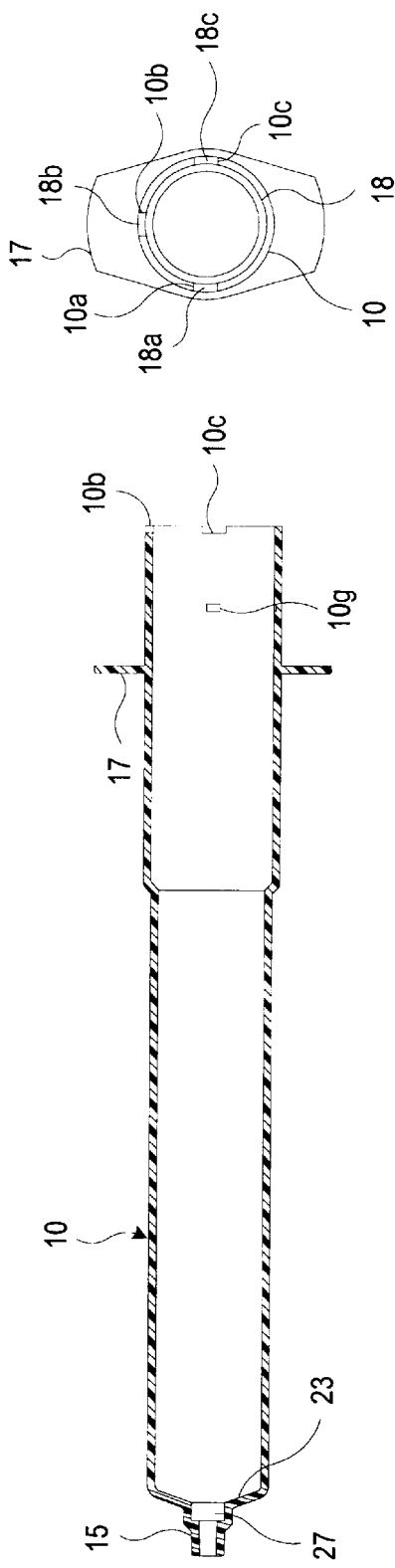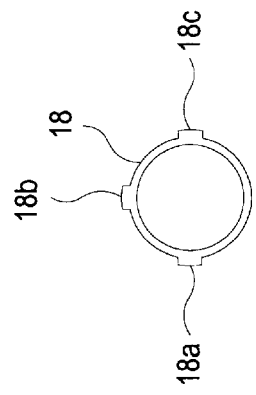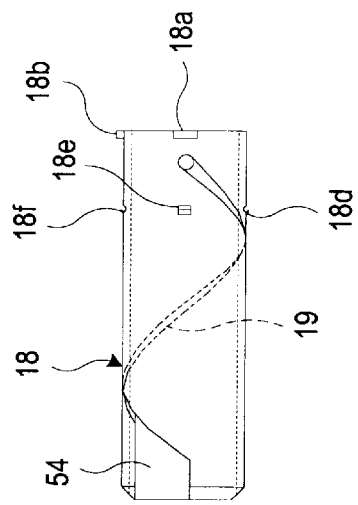
FIG. 7
FIG. 9
FIG. 6
FIG. 8

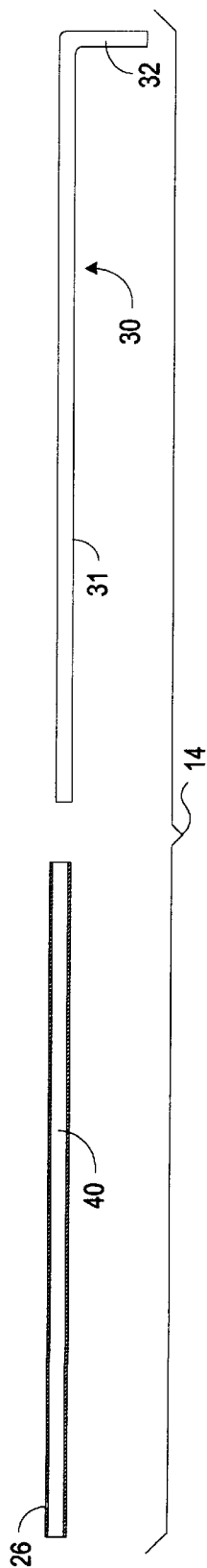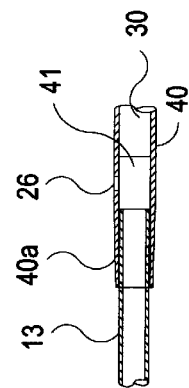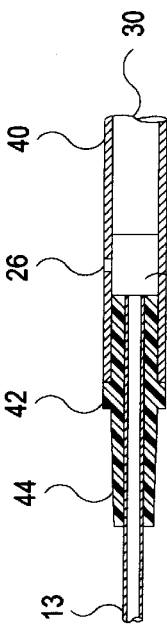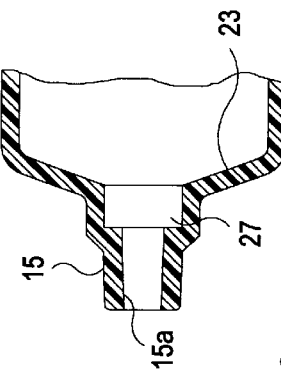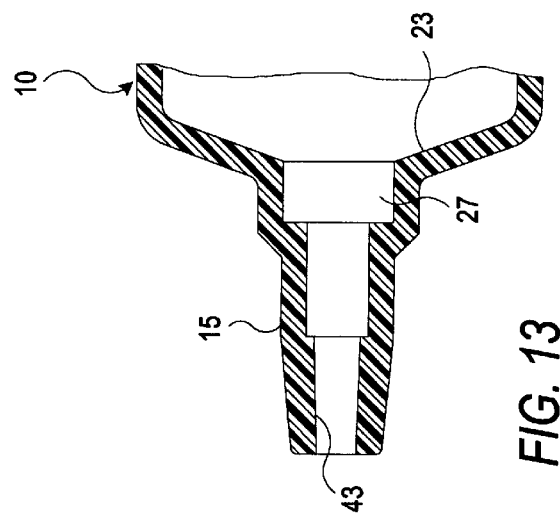

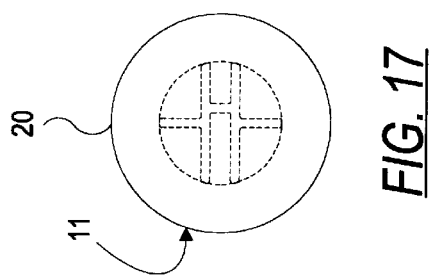
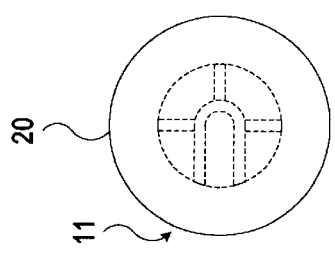
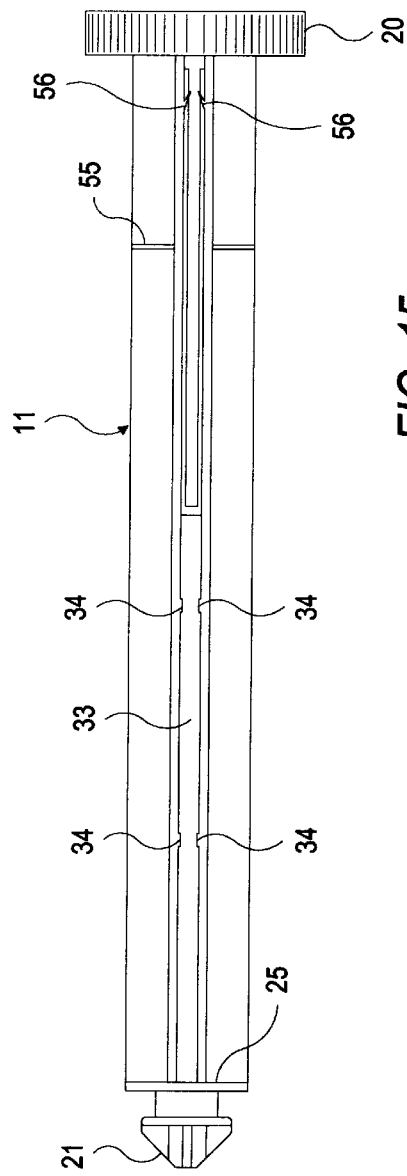
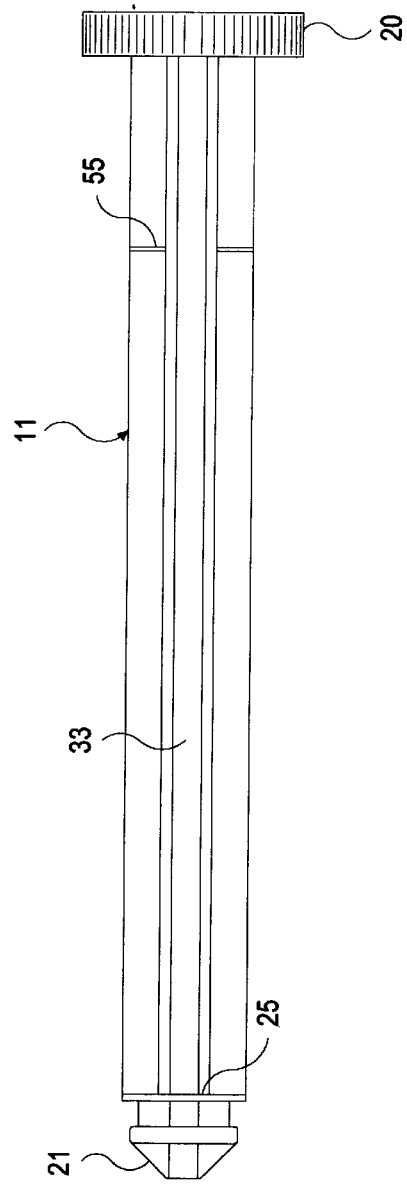
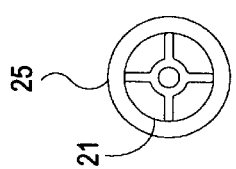
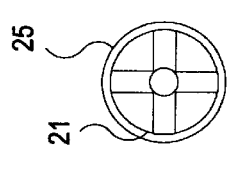

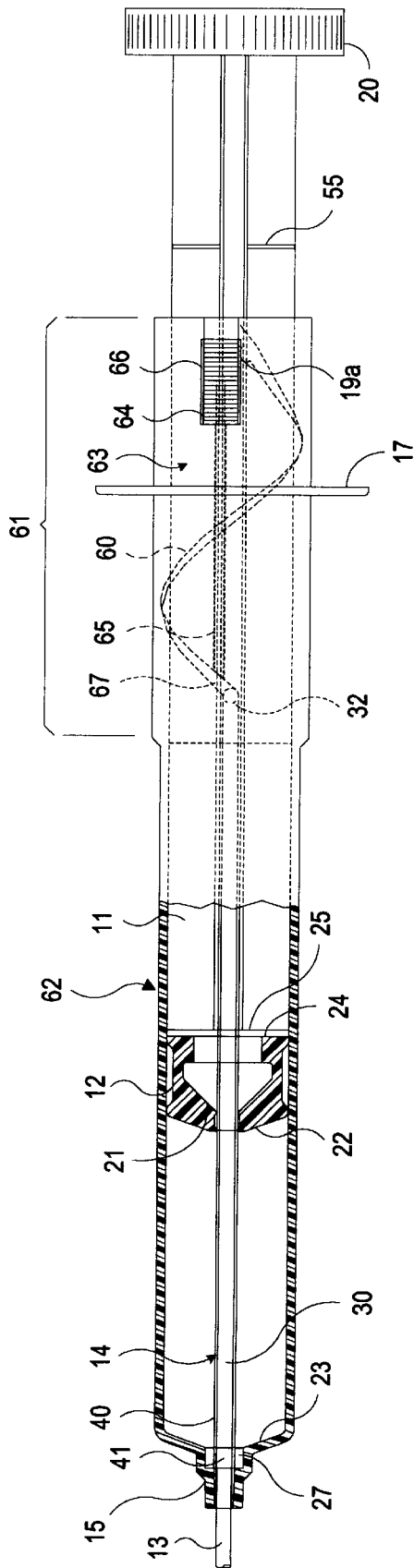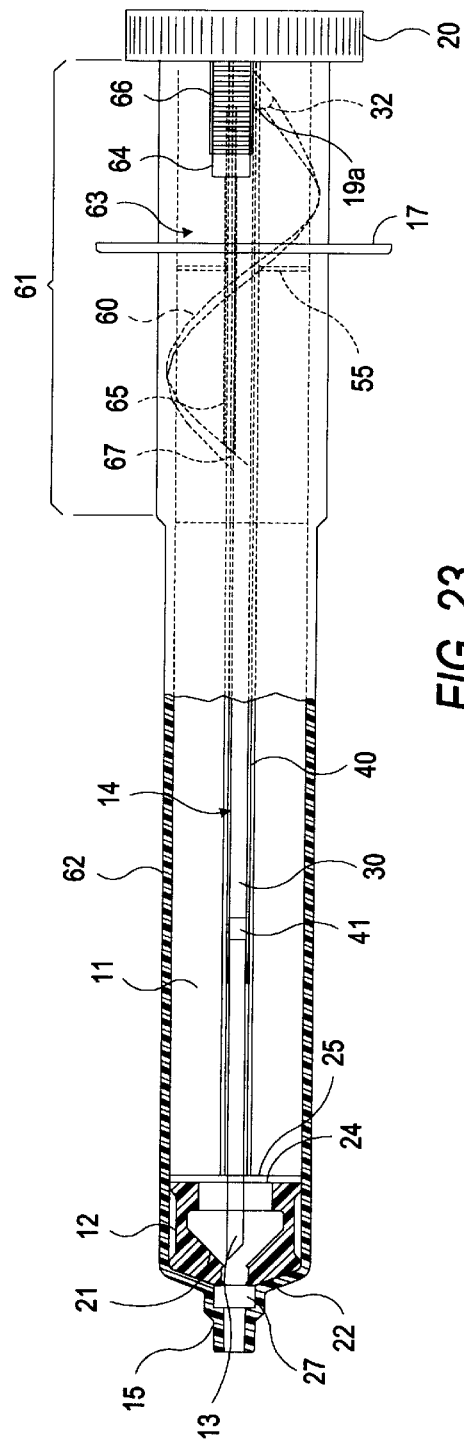
FIG. 22
FIG. 23

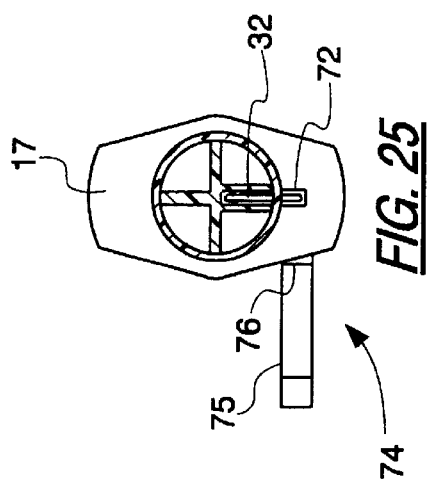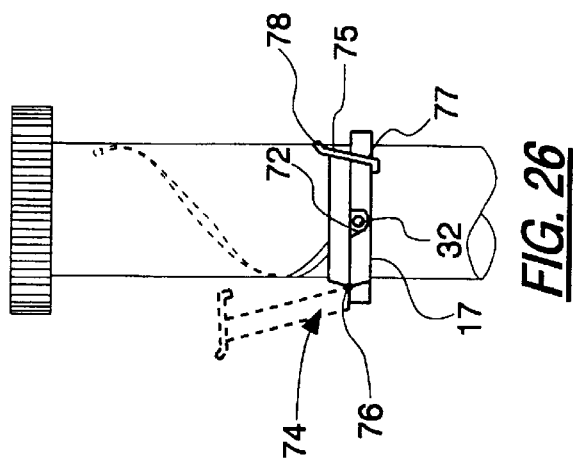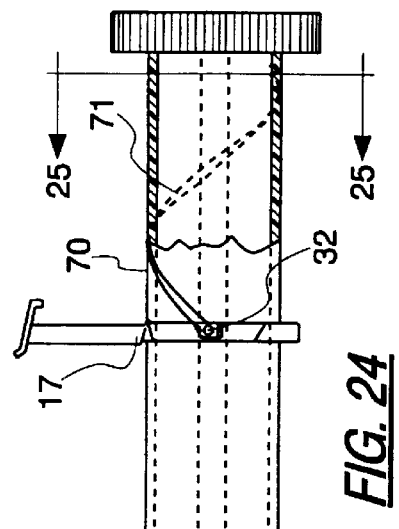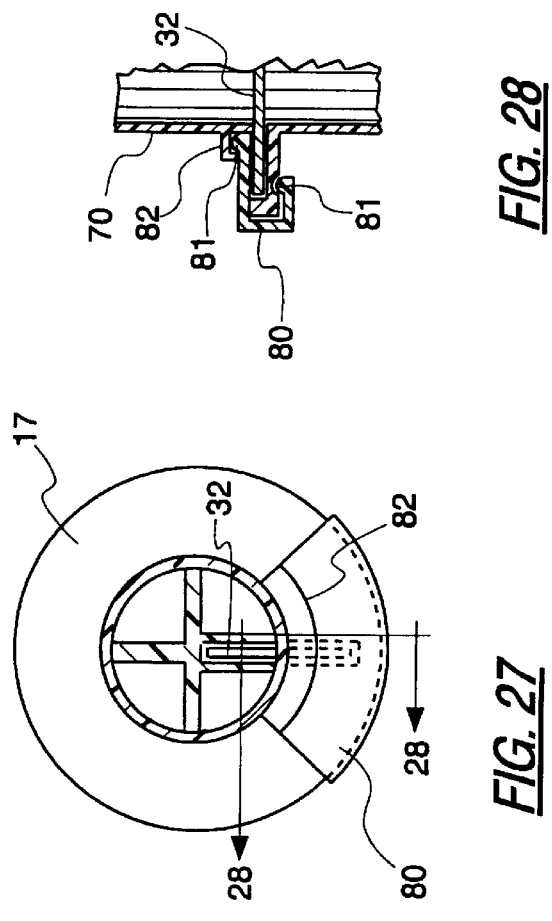

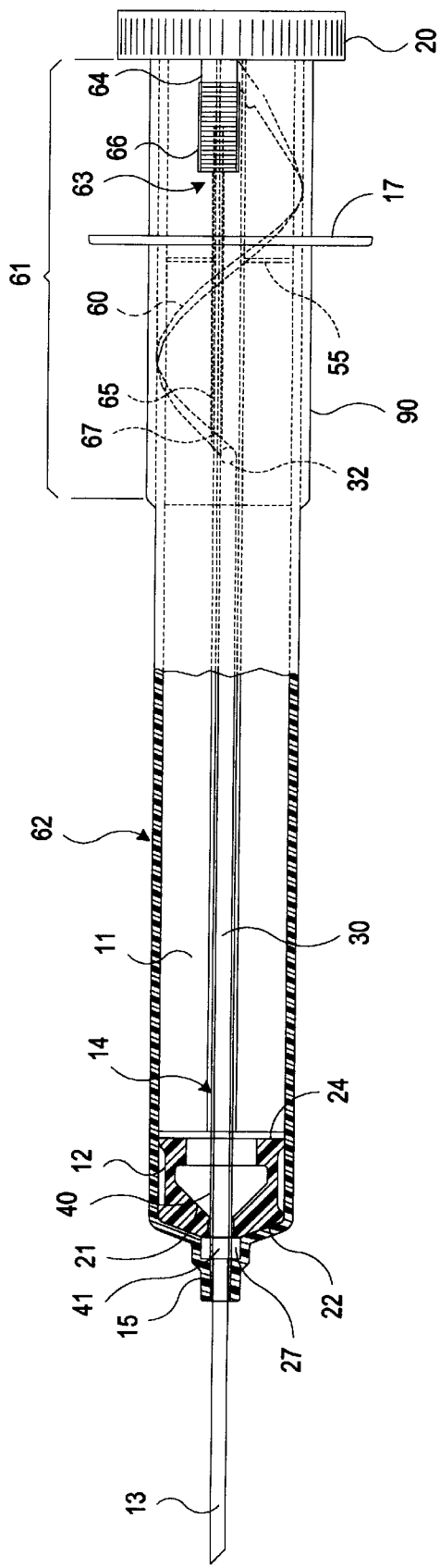
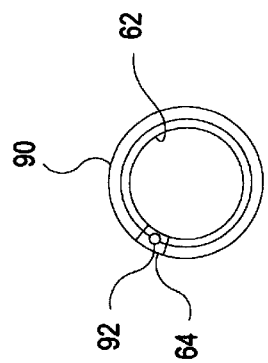
FIG. 29
FIG. 30

HYPODERMIC NEEDLE ASSEMBLY

CROSS-REFERENCES TO RELATED APPLICATIONS

This application is a continuation-in-part of U.S. patent application Ser. No. 08/494,283 filed Jun. 23, 1995, now U.S. Pat. No. 5,643,222, which in turn is a continuation-in-part of U.S. patent application Ser. No. 08/229,811, filed Apr. 19, 1994, now U.S. Pat. No. 5,514,100, which in turn is a division of application Ser. No. 08/111,372, filed Aug. 23, 1993, now U.S. Pat. No. 5,338,311.

FIELD OF THE INVENTION

The present invention generally relates to hypodermic needles. In particular, the present invention relates to a needle-syringe assembly which conceals the sharp point of the hypodermic needle following use.

BACKGROUND OF THE INVENTION

A hypodermic needle has many applications in modern medicine. One application is to fit the hypodermic needle onto a syringe and to then insert the needle into a person's body for intramuscular, subcutaneous, or intravenous injection of medications. A hypodermic needle entering into a patient's body is invariably contaminated by the patient's blood and body fluids. Following use of the needle, the needle presents a risk to physicians, nurses, and other health care personnel because the needle might transmit an infection or disease to such personnel if it were to accidently puncture them. Thus, health care personnel are in constant danger of contracting infections and diseases, some of which may be deadly. Other potential victims of accidental needle punctures include sanitation workers which later dispose of garbage containing the hypodermic needle. The diseases which may be transmitted by a contaminated hypodermic needle include Immune Deficiency Virus, Hepatitis, Rabies, Kure, Encephalitis, and Arbor viruses. The outcome of contracting one of these diseases is often fatal because there are no known cures for any of these diseases. Often a needle puncture in a person's skin is so trivial that it remains unrecognized until the person becomes seriously ill.

The problem of suffering accidental needle punctures is well recognized. As a result, enormous inventive effort has been devoted to concealing the sharp needle point of hypodermic needles. One such effort is described in the present applicant's U.S. Pat. No. 5,338,311, issued Aug. 16, 1994.

SUMMARY OF THE INVENTION

A primary object of the present invention is to improve the needle-syringe assembly described in the aforementioned U.S. Pat. No. 5,338,311.

One specific object of this invention is to provide an improved needle-syringe assembly which provides good structural stability for the mechanism that is used to retract the needle after it has been used.

Yet another object of the present invention is to provide such an improved needle-syringe assembly which facilitates fabrication, and reduces the cost, of the assembly.

Still another object of the present invention is to provide such an improved needle-syringe assembly which facilitates the operation of the assembly, particularly when it is desired to retract the needle prior to disposing of the needle-syringe assembly.

Another object of the present invention is to provide such an improved needle-syringe assembly which improves the acceptability of the assembly by providing an external appearance which is virtually the same as that of conventional hypodermic needle assemblies which do not provide for needle retraction.

A further object of the invention is to provide such an improved needle-syringe assembly that has the same length as conventional hypodermic needle assemblies which do not provide for needle retraction.

Other objects and advantages of the invention will become apparent upon reading the following detailed description and upon reference to the accompanying drawings.

In accordance with the present invention, the foregoing objectives are realized by providing a needle-syringe assembly, operable in a normal mode and convertible to a retraction mode, comprising an elongated, generally cylindrical barrel forming a hollow nozzle located at the distal end of the barrel and opening into the interior of the barrel; a plunger slidably mounted in the barrel and forming a longitudinal cavity extending between the distal end and the proximal end of the plunger; a needle holder slidably mounted in the longitudinal cavity of the plunger; guide means forming a spiral channel extending along a proximal end portion of the barrel for retracting the needle holder within the barrel in response to relative rotational movement between the barrel and the plunger; and latching means on the barrel for latching and unlatching the needle holder at the distal end of the spiral channel.

BRIEF DESCRIPTION OF THE DRAWINGS

FIG. 1 is a side elevation, partially in section, of a needle-syringe assembly embodying the present invention;

FIG. 2 is a section taken generally along line 2—2 of FIG. 1;

FIG. 2a is a section taken generally along line 2a—2a in FIG. 1, with the plunger removed;

FIG. 3 is a plan view of the latching element included in the needle-syringe assembly of FIG. 1;

FIG. 4 is the same view shown in FIG. 1, but with the plunger partially retracted;

FIG. 5 is the same view shown in FIG. 1 with the needle holder in the retracted position and the plunger in its fully advanced position;

FIG. 6 is a reduced longitudinal section of the barrel of the needle-syringe assembly of FIG. 1;

FIG. 7 is an end elevation of the barrel of FIG. 6;

FIG. 8 is a reduced side elevation of the guide sleeve in the needle-syringe assembly of FIG. 1;

FIG. 9 is an end elevation of the guide sleeve of FIG. 8;

FIG. 10 is an exploded view of the needle holder assembly in the needle-syringe assembly of FIG. 1;

FIG. 11 is an enlarged section of the distal end portion of the left-hand element of the needle holder assembly as shown in FIG. 10;

FIG. 12 is an enlarged section of the distal end portion of the barrel that receives the needle holder assembly of FIGS. 10 and 11;

FIG. 13 is an enlarged section of the distal end portion of a modified barrel for receiving a modified needle-holder assembly;

FIG. 14 is a fragmentary longitudinal section of the distal end portion of a modified needle holder assembly for use with the modified barrel shown in FIG. 13;

FIG. 15 is a side elevation of the plunger in the needle-syringe assembly of FIG. 1;

FIG. 16 is an end elevation of the distal end of the plunger of FIG. 15;

FIG. 17 is an end elevation of the proximal end of the plunger of FIG. 15;

FIG. 18 is a side elevation of a modified plunger for use in the needle-syringe assembly of FIG. 1;

FIG. 19 is an end elevation of the distal end of the plunger of FIG. 18;

FIG. 20 is an end elevation of the proximal end of the plunger of FIG. 18;

FIG. 22 is the same view shown in FIG. 21 with the plunger partially retracted;

FIG. 23 is the same view shown in FIG. 21 with the needle and needle holder retracted and the plunger in its fully advanced position;

FIG. 24 is a side elevation, partially in section, of another modified needle-syringe assembly embodying the present invention;

FIG. 25 is an end elevation of the proximal end of the assembly shown in FIG. 24;

FIG. 26 is a side elevation of the latch mechanism included in the assembly of FIGS. 24 and 25;

FIG. 27 is an end elevation of the proximal end of another modified needle-syringe assembly embodying the invention;

FIG. 28 is a section taken generally along line 28—28 in FIG. 27;

FIG. 29 is a side elevation, partially in section, of a modified syringe embodying the invention;

FIG. 30 is an end elevation of the proximal end of the barrel in the syringe of FIG. 29, with the latching element removed;

Figure 31:
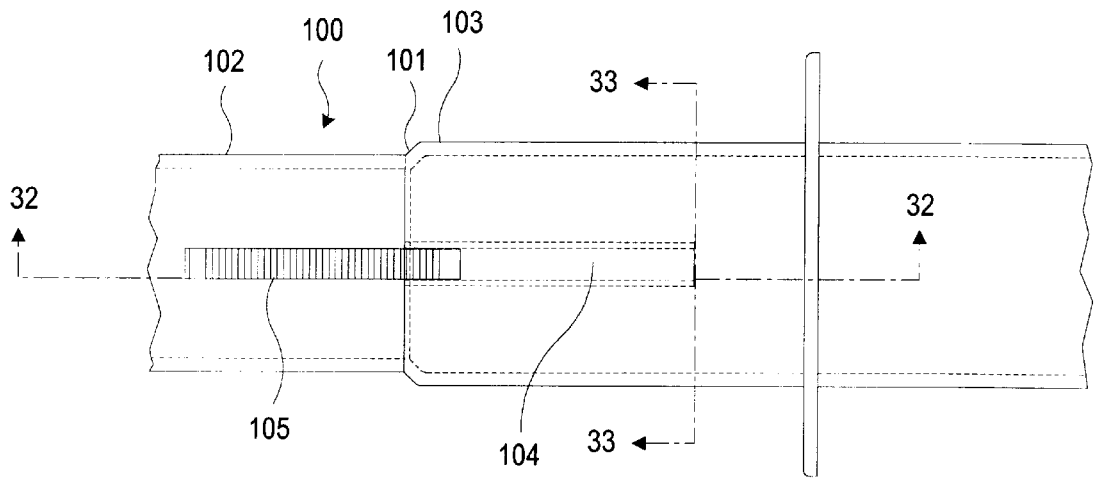
FIG. 31 is a partial side elevation of a modified barrel and latch design.

PIG. 32 is a section taken generally along line 32—32 in FIG. 31; and

Figure 33:
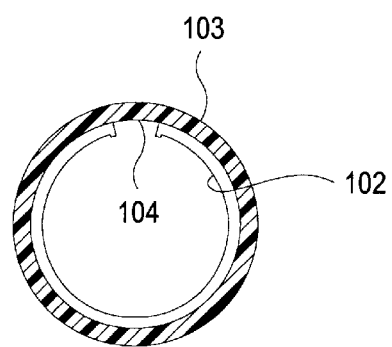

FIG. 33 is a section taken generally along line 33—33 in FIG. 31.

DETAILED DESCRIPTION OF THE PREFERRED EMBODIMENTS

While the invention is susceptible to various modifications and alternative forms, specific embodiments thereof have been shown by way of example in the drawings and will herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

In order to satisfy the best mode requirement for this disclosure, several different modes of the invention, each with its own unique features and alternate embodiments, are described. Permutations and combinations of these features will, however, lead to further modes.

Turning now to the drawings, FIGS. 1–12 and 15–17 illustrate a needle-syringe assembly including a barrel 10, a plunger 11, a hollow plunger cap 12, a hypodermic needle 13, and a needle holder 14. The barrel 10 is a hollow cylinder which terminates in a hollow tapered nozzle 15 at the distal end thereof, and has a slightly enlarged diameter along a proximal end portion 16. The interior of the nozzle 15 communicates with the hollow interior of the tubular body portion of the barrel 10. An outwardly extending flange 17 near the proximal end of the barrel 10 facilitates gripping of the barrel with the user's fingers when it is desired to move the plunger 11 relative to the barrel 10.

The purpose of the enlarged diameter of the proximal end portion 16 of the barrel 10 is to accommodate a sleeve 18 incorporating a spiral slot 19 within its wall and without encroaching on the inner diameter of the entire syringe. As will be described below, this spiral slot 19 provides an internal retraction track for the needle holder 14 and the hypodermic needle 13. The sleeve 18 and its spiral slot 19 extend along a sufficient length to accommodate retraction of the needle holder 14 through a distance that is sufficient to draw the entire length of the needle 13 inside the barrel 10, as described in more detail below. The outer surface of the barrel 10 preferably contains graduations (not shown) indicating the volume level of fluid in the barrel. These graduations take into account the volume of the internal components such as the needle holder 14.

The proximal end of the plunger 11 forms a knob 20 that can be grasped by a user to effect linear or rotary movement of the plunger 11 relative to the barrel 10. The periphery of the knob 20 is serrated to facilitate gripping of the knob for rotary movements of the plunger. The distal end of the plunger 11 forms a head 21 to accommodate the hollow rubber plunger cap 12. The outside diameter of the resilient cap 12 is reduced in the central portion so that the cap engages the inside wall of the barrel 10 only at the pliable margins of the ends of the cap. The diameter of the engaging end portions of the cap 12 is slightly larger than the inside diameter of the barrel 10 so that the cap presses firmly against the inside wall of the barrel to form an air-tight and liquid-tight seal at the cap/barrel interface. The inner margins of the cap 12 make a similar tight contact with the outer surface of the needle holder 14. The distal end 22 of the cap 12 is conical to conform to the conical distal end 23 of the inside surface of the barrel 10 when the plunger 11 is fully advanced within the barrel.

The head 21 of the plunger 11 is configured to fit tightly within the hollow plunger cap 12. With the cap 12 locked onto the head 21 of the plunger, the flat proximal end 24 of the cap abuts the flat surface of a circular disc 25 at the base of the plunger head 21. Due to the air-tight and liquid-tight seal between the plunger cap 12 and the barrel 10, as well as the needle holder 14, advancing movement of the plunger 11 inside the barrel 10 creates pressure in the interior of the barrel between the plunger cap and the distal end of the barrel. Similarly, retracting movement of the plunger 11 creates a vacuum in that portion of the barrel interior.

The hypodermic needle 13 is mounted on the distal end of the elongated needle holder 14, which is detachably interlocked to the barrel 10. Prior to use of the needle-syringe assembly, the needle 13 is covered by a protective cap (not shown) which prevents needle pricks and preserves sterility prior to use. Both the needle 13 and the distal portion of the needle holder 14 are hollow, and the interior of the hollow needle 13 communicates with the interior of the hollow distal portion of the needle holder 14. The needle holder 14 further communicates with the interior of the barrel 10 through an aperture 26 in the side wall of the hollow portion of the needle holder 14 (FIGS. 10 11 and 14). Prior to and during use of the needle-syringe assembly for injection of medicine or withdrawal of blood (hereafter referred to as "normal use"), the aperture 26 is positioned at the base of the barrel nozzle 15 FIG. 5), sometimes within a small cylindrical cavity 27. The aperture 26 permits blood or medicine to enter or exit from the barrel 10 via the needle holder 14 and the needle 13.

During normal use of the needle-syringe assembly, the needle holder 14 is locked to the barrel 10, and the plunger 11 and its cap 12 are free to slide longitudinally back and forth along the needle holder. The needle holder 14 includes a metal tube 40 and an L-shaped metal rod 30 having a longitudinal body portion 31 extending coaxially through the tube 40 to the aperture 26, and a lateral arm 32 extending radially across the barrel 10 at the proximal end of the rod 30.

To permit relative sliding movement between the plunger 11 and the needle holder 14 in the longitudinal direction, the needle holder is mounted in a longitudinal channel 33 formed as an integral part of the plunger 11. Multiple pairs of resilient retaining elements 34 (FIG. 15) project toward each other from the opposed walls of the channel 33 to hold the needle holder 14 within the channel. These retaining elements 34 are deflected into adjacent recesses during insertion of the needle holder 14 into the channel 33, and then the elements 34 spring back to their original positions after the needle holder is in place. It will be noted that the opposed walls of the channel 33 extend all the way to the inside wall of the barrel 10 (see FIG. 17), thereby constraining the lateral arm 32 of the needle holder against any angular or rotational displacement relative to the plunger 11. That is, the plunger 11 and the needle holder 14 can rotate only in unison with each other, although they are free to move independently of each other in the longitudinal direction. At the proximal end of the needle holder, a locking detent (described below) locks the arm and plunger together to prevent relative longitudinal movement after retraction is complete.

A major portion of the stainless steel rod 30 is encased in a stainless steel hypodermic tube 40 which extends beyond the distal end of the rod 30 and overlaps a portion of the needle 13. The opposed ends of the needle 13 and the rod 30 are separated slightly from each other, and the intervening space is surrounded by the stainless steel tube 40 to form a cavity 41 through which fluids pass between the hollow interiors of the needle 13 and the barrel 10. The aperture 26 mentioned previously is formed in this portion of the tube 40.

To lock the needle holder 14 to the barrel 10, the outer surface of the distal end portion of the metal cover tube 40 is ground (e.g., by centerless grinding) to form a tapered surface 40a which mates with a complementary tapered surface 15a on the inside wall of the barrel nozzle 15. These tapered surfaces 40a and 15a are conventionally known as locking luer tapers, and the angle of the taper (typically 6% of the diameter) is conventionally known as a locking taper angle. In a preferred embodiment, the taper has a length between about 0.185 and about 0.250 inch with a diameter of 0.094 inch at one end and a diameter of 0.082 inch at the other end.

The locking surfaces 15a and 40a are engaged during assembly of the needle syringe, when the plunger 11 and needle holder 14 are inserted into the barrel 10 through the open proximal end of the barrel. The resultant locking luer taper can be released only by the application of simultaneous axial and rotational forces.

The proximal end of the needle holder 14 is also locked to the barrel 10, via the lateral arm 32 of the metal rod 30. This arm 32 extends radially beyond the plunger and fits into the spiral slot 19 in the sleeve 18. The arm 32 can be locked to the barrel 10 at either end of the spiral slot 19 and, when so locked, permits only reciprocal linear movement of the plunger 11, to create vacuum to withdraw medication or blood and pressure to deliver medication to the patient via the hypodermic needle. When the arm 32 is locked at either end of the slot 19, the plunger 11 cannot be rotated within the barrel 10.

When the user desires to retract the hypodermic needle 13 within the barrel-plunger assembly, a mechanical latch 50 is manually actuated to unlock the arm 32 and thereby permit rotation of the plunger 11 relative to the barrel 10. This relative rotation retracts and locks the needle-needle holder assembly within the barrel-plunger assembly. For the needle and needle holder to be moved to the retracted position, the plunger 11 can be in any desired position, e.g., to permit blood or medication to be retained in the syringe.

The preferred latch mechanism 50 of FIGS. 1–5 includes an arcuate locking plate 51 and an integral handle 52 mounted for sliding movement within a short longitudinal slot 53 in the wall of the barrel 10. The free end of the plate 51 is angled to match the slope of the side walls of the spiral slot 19, and the plate slides back and forth within a slot 54 formed in the sleeve 18 and opening into the slot 19 adjacent the distal end of the slot. The inner and outer radii of the plate 51 match those of the sleeve 18 (see FIG. 2) to ensure that the locking plate 51 fits precisely into the slot 54 in the sleeve 18 and cannot fall inside the barrel cavity to obstruct movement of the plunger 11, in either the locked or unlocked position of the latch. As can be seen in FIG. 2, the locking plate 51 and the handle 52 are offset from each other in the radial direction so that the handle rides on the outer surface of the barrel 10. This outer handle surface is serrated to facilitate movement thereof with the user's finger or thumb.

The latch 50 can be opened or closed by linear movement of the locking plate 51 via the handle 52. During normal use, the needle holder arm 32 is positioned at the distal end of the spiral slot 19 and the locking plate 51 is advanced into the spiral slot 19 to close the slot and retain the arm 32 at the distal end of the slot 19. This locks the needle holder 14 in the normal operative mode in which only linear reciprocal movement of the plunger 11 is permitted. Because the locking plate 51 blocks the spiral slot 19, the needle holder 14 cannot rotate and thus cannot travel along the spiral slot 19 for retraction of the hypodermic needle 13. When it is desired to retract the needle, the latch handle 52 is retracted toward the distal end of the syringe, thereby opening the spiral slot 19 and permitting rotation of the plunger 11 and retraction of the needle holder 14 by movement of the arm 32 along the spiral slot.

It will be appreciated that when the latch 50 is retracted to open the spiral slot 19 and thereby unlock the arm 32, the plunger can be in any desired longitudinal position. That is, the plunger can be fully advanced, fully retracted, or at any intermediate position. This is advantageous because it might be desired to retract the needle after only a portion of a dose of medication has been injected into the patient, or it might be desired to retain a portion of a blood sample withdrawn from a patient within the syringe. To prevent the leakage of any fluid contained within the syringe at the time the needle is retracted, it is preferred to provide a latex seal (not shown) at the end of the nozzle 15.

To ensure retention of the end portion of the arm 32 within the spiral slot 19 during retracting movement of the needle holder 14, the plunger 11 includes an integral circular retaining plate 55. The diameter of this plate 55 matches the inside diameter of the guide sleeve 18 so that it tends to maintain the desired circular shape of the inside wall of the sleeve 18. Stresses exerted on the wall of the barrel during use can tend to distort the desired circular configuration of the sleeve 18, and if the distortion becomes large enough, the arm 32 can escape from the spiral slot 19. With the retainer plate 55 riding on the inside wall of the sleeve 18, however, such excessive distortion is prevented, and thus retention of the arm 32 within the spiral slot 19 is ensured. Of course, in addition to the retainer plate 55, the longitudinal ribs of the plunger also glide on the inside wall of the sleeve 18 at approximately 90° intervals from each other, and thus further ensure that the sleeve 18 retains its desired circular configuration.

During normal use of the needle-syringe assembly, the barrel 10 and the needle holder 14 are held stationary, and the plunger 11 is free to move relative to both the barrel 10 and the needle holder 14. Advancing movement of the plunger 11 is limited by contact of the plunger cap 12 with the end wall of the barrel 10, as shown in FIG. 1. Retracting movement of the plunger 11 is limited by contact of the plunger disc 25 with the arm 32. If desired, stop members may be provided on the inside surface of the barrel to engage the disc 25 on the distal side of the latch opening, to further protect against the leakage of fluids through the latch opening in the barrel wall. The needle holder 14 is locked to the barrel 10 by virtue of the taper lock between the distal portion of the needle holder and the barrel nozzle 15, and the locking engagement of the lateral arm 32 in the wall of the barrel. Alternatively, the needle holder can be locked to the nozzle by a threaded connection, as described in more detail in U.S. Pat. No. 5,643,222. The plunger 11 is also free to move longitudinally relative to the needle holder 14, as illustrated in FIG. 4, because the needle holder is not locked to the plunger in that direction. The locking of the lateral arm 32 to the barrel wall prevents rotational movement of the plunger as well as the needle holder, and also prevents the plunger from being accidentally pulled out. As long as the lateral arm 32 of the needle holder is locked to the barrel wall, the needle-syringe assembly is in its normal operating mode.

Following normal use of the needle-syringe assembly, the needle 13 can be retracted into the plunger 11 and the barrel 10. This requires axial movement of the needle holder 14 within the barrel 10 toward the proximal end thereof, which in turn requires that the needle holder 14 be unlocked for movement along the spiral slot 19. Thus, to initiate retraction of the needle holder 14, the arm 32 is unlocked by retracting the locking plate 51.

After the latching plate 51 has been retracted, the plunger knob 20 is turned to rotate the plunger 11 clockwise (as viewed from the proximal end) relative to the barrel. As the plunger is rotated, the needle holder 14 rotates in unison with the plunger because the arm 32 is captured between the opposed parallel walls of the channel 33 in which the needle holder is mounted in the plunger. Rotation of the needle holder 14 relative to the barrel (1) retracts the needle holder within the plunger by the camming action of the wall of the spiral slot 19 acting on the arm 32, and (2) releases the locking luer taper at the distal end of the barrel nozzle 15 due to the resulting compound rotational and longitudinal forces applied to the tapered surfaces 15a and 40a. As rotation continues, the arm 32 traverses the entire length of the spiral slot 19, thereby retracting the entire needle holder 14 through a corresponding axial distance within the plunger 11 (see FIG. 5). Of course, the needle 13 is retracted along with the needle holder 14, and thus the needle is retracted completely within the barrel nozzle 15 and the plunger 11, as illustrated in FIG. 5.

In the illustrative embodiment, the spiral slot 19 is formed in a sleeve 18 fitted inside a distal end portion of the barrel 10, and attached to the barrel. The spiral slot preferably has a constant rate of curvature along its length. The portion of the barrel 10 that receives the sleeve 18 has a slightly larger diameter than the central portion of the barrel, and the sleeve 18 has the same inside diameter as the central portion of the barrel. Alternatively, a spiral channel can be molded as a part of the inside wall of the end portion of the barrel that has the slightly larger diameter. The illustrative syringe need not be any longer than a conventional syringe because conventional syringes are made longer than required to provide more than the desired fluid volume, so as to avoid inadvertent withdrawal of the plunger and the resultant spillage of the syringe contents. The extra barrel length also accommodates the user's fingers in the space between the plunger knob and the finger flanges. The present invention permits the extension of the barrel length in this area to be used for the needle-retracting mechanism.

To attach the sleeve 18 to the barrel 10, three tabs 18a, 18b, 18c extend radially outwardly from the sleeve 18 into complementary notches 10a, 10b, 10c in the distal end of the barrel. To lock the sleeve to the barrel longitudinally as well as rotationally, four fingers 18d–18g on opposite sides of the sleeve 18 snap into complementary recesses 10d–10g on the inside wall of the barrel.

At the distal end of the spiral slot 19, the end of the arm 32 snaps into a detent notch 19a (FIGS. 1, 4 and 5) formed by the walls of the slot so that the user feels the end of the needle retraction, as a click. Then if the user attempts to turn the plunger knob 20 in the opposite direction, such attempt is met with firm resistance. This is a safety feature to prevent the needle from being returned beyond the end of the barrel nozzle, and to discourage re-use of the needle.

A pair of resilient locking fingers 56 (FIG. 15) are formed in the opposed walls of the channel 33 near the proximal end thereof to prevent the plunger 11 from being withdrawn from the barrel 10 after the needle holder 14 has been retracted. The arm 32 deflects the fingers 56 into adjacent recesses as the arm is retracted past the fingers, but the arm 32 then blocks any effort to retract the plunger 11 over the needle holder 14.

FIGS. 18–20 illustrate a modified plunger for use with a needle holder having a larger diameter than the needle holder used with the plunger of FIGS. 15–17. For example, the relatively thin needle holder of FIG. 11 can be used in the plunger of FIGS. 15–17, and the larger-diameter needle holder of FIG. 14 can be used in the plunger of FIGS. 18–20. It will be noted that the passageway 33 is wider in the plunger of FIGS. 18–20 than in the plunger of FIGS. 15–17. Similarly, the hole that extends through the distal end of the plunger is also larger in FIG. 19 than it is in FIG. 16. Certain of the details of the plunger of FIGS. 15–17, such as the retaining elements 34 and the fingers 56, have not been included in the illustration of the plunger in FIGS. 18–20, but it will be understood that similar features may be included in both plungers.

To operate the needle-syringe assembly, the protective cap (not shown) is removed from the needle 13, and the required amount of medication is aspirated into the barrel 10. Next, the injection site on the body of a patient is determined and the skin is cleaned with an antiseptic solution. Following percutaneous entry of the needle into the patient, location of the needle tip in the vein is confirmed by aspirating a small amount of blood into the transparent barrel 10. The plunger 11 is then advanced to force the medication from the barrel 10 into the vein. After the medication is administered, the needle 13 is withdrawn from the patient, the latch handle 52 is retracted to open the spiral channel 19, and the plunger knob 20 is rotated clockwise until the user feels the arm 32 snap into the detent notch 19a at the proximal end of the spiral slot 19. The spiral slot 19 may alternatively be configured to require counterclockwise, instead of clockwise, rotation of the plunger knob 20. With the needle 13 completely retracted inside the barrel 10, the needle-syringe assembly can be safely discarded in its entirety.

It can be seen from the foregoing description that the needle-syringe assembly performs all the conventional functions of injection syringes and yet, upon completion of injection, the hypodermic needle 13 is concealed within the barrel 10. The needle-syringe assembly can receive and disperse medications any number of times for a given patient by reciprocal longitudinal movement of the plunger 11 within the barrel 10. Another advantage of the needle-syringe assembly is that its design prevents the plunger 11 from slipping out of the barrel 10 during normal use of the assembly.

The needle-syringe assembly of this invention is easy to manufacture, cost-effective, and easy to use in the field. The parts can all be made by conventional plastic molding and using readily available metal needle stock. The plastic parts can be made by injection molding medical grade polymers such as polypropylene. The; plunger seal or cap can be molded from natural or synthetic elastomeric polymers. The guide sleeve with the spiral slot can be molded and press fit into the wide end of the barrel. The spiral channel on the inside wall of the barrel can be molded with rotating cores which are removed by rotating them while withdrawing them from the 30 molded part.

The final assembly is compact because the needle holder 14 is retracted directly into the plunger 11 itself, and thus the plunger 11 need not be fully extended for needle retraction to occur. When discarded following use, the needle-syringe assembly contributes minimally to the bulk of refuse. Since retraction of the needle 13 is effected by turning the plunger knob 20 at the proximal end of the assembly, the hand of a user does not come into the vicinity of the needle point, thereby minimizing the possibility of a needle prick during retraction. Moreover, the assembly employs substantially the same number of components as conventional syringes, and does not require additional guards, sheaths, sleeves, springs, etc. to conceal the needle following use.

FIGS. 13 and 14 illustrate a modified construction for locking the distal end of the needle holder 14 to the barrel nozzle 15. In this design the distal end of the tube 40 abuts a shoulder on a plastic insert 42 bonded to that portion of the needle that is within the barrel nozzle 15. This insert 42 fits tightly against the inside surface of the nozzle 15, and these mating surfaces of the insert 42 and the nozzle 15 are tapered to form a conventional locking luer taper (typically 6% of the diameter). Specifically, the inside surface of the nozzle 15 forms a locking female luer taper 43, and the outside surface of the insert 42 forms a locking male luer taper 44. In the preferred embodiment, the inside diameter of the nozzle 15 varies from 0.0737 inch at the proximal end of the taper to 0.0625 inch at the distal end of the taper. The longitudinal distance between these two inside diameters is 0.1875 inch. The diametric difference between the two diameters forms a locking luer taper in the nozzle 15.

Figure 21:
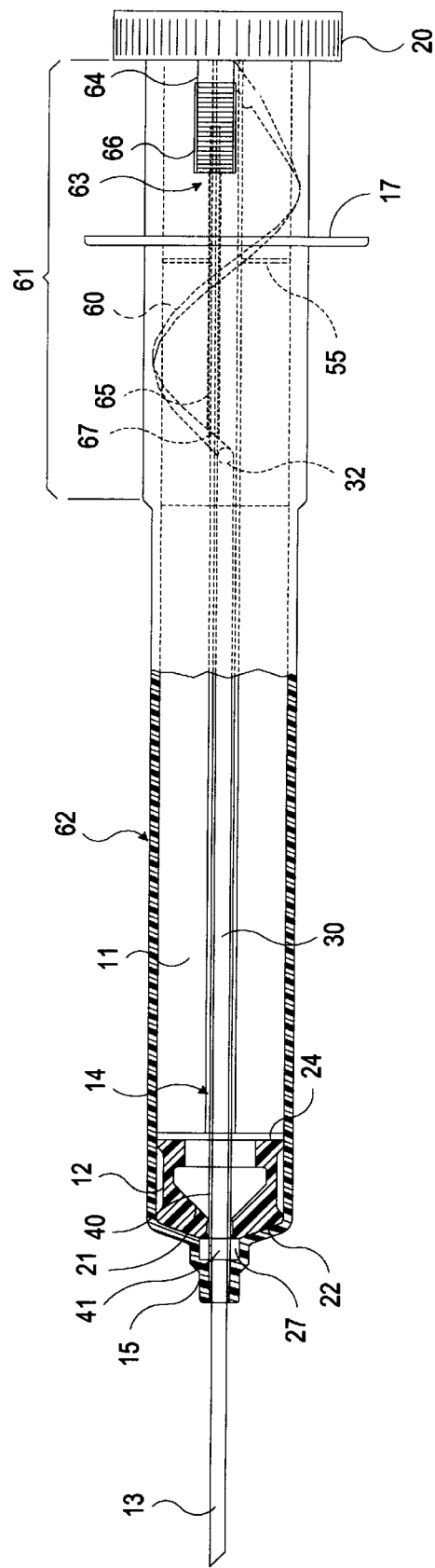
FIG. 21 is a side elevation, partially in section, of a modified needle-syringe assembly embodying the present invention.

A modified embodiment and latch mechanism is shown in FIGS. 21–23. In this embodiment, a spiral channel 60 is integrally molded on the inner surface of a proximal end portion 61 of a barrel 62. To accommodate the spiral channel 60, the wall thickness of the barrel 62 is increased in the end portion 61. Internal molding of the spiral channel 60 is possible when mold cores are rotated while they are pulled from the mold cavity used to form the barrel 62. A latch mechanism 63 is mounted in a straight longitudinal slot 64 that opens through the proximal end of the barrel 62 and continues as a straight longitudinal channel 65 on the inside wall of the barrel 62. The spiral channel 60 preferably extends less than 360 degrees around the circumference of the barrel 62, and opens through the proximal end of the barrel. This avoids interference between the spiral slot 60 and the channel 65. The slot 64 receives a serrated latch handle 66 that fits precisely into the slot 64 but is shorter than the slot in the axial direction and mates with recesses in the side walls of the slot 64. The handle 66 is molded on a metal pin 67 that extends distally beyond the slot 64 and along the entire length of the channel 65 which opens into the end portion of the spiral channel 60 adjacent the distal end thereof. The external surface of the handle 66 is serrated to facilitate frictional gripping for capture and release of the needle holder arm by the latching pin 67.

During assembly, the right-angle needle holder arm 32 is engaged in the spiral channel 60 through its open end, and then the end of the spiral channel is closed by heat crimping. The needle holder 14 is advanced until the arm 32 reaches the distal end of the spiral channel 60. At this location the needle holder arm 32 is locked in its advanced position in the spiral channel 60 by advancing the handle 66 so that the pin 67 enters and blocks the spiral channel 60. This prevents rotation of the needle holder 14 so that it cannot be moved along the spiral channel 60. Linear movements of the plunger 11 do not affect the pin engagement that is perpendicular to the spiral. When it is desired to retract the needle 13, the handle 66 is retracted to the proximal end of the barrel 62 to retract the pin 67 and open the spiral channel 60, thereby permitting rotation of the plunger 11 and resultant retraction of the needle holder 14 via the spiral channel.

Yet another modified embodiment and latch mechanism is shown in FIGS. 24–26. In this embodiment, the needle holder 14 with a relatively short hypodermic needle 13 is engaged in a barrel 70 having the normal finger flange 17 and extended barrel length to reach the plunger knob 20. In this embodiment, the spiral track for retracting movement of the arm 32 is formed by a spiral slot 71 which extends through the entire thickness of the barrel wall. It will also be noted that the barrel 70 has a uniform wall thickness, and a uniform outside diameter, along its entire length, including that portion of the barrel in which the spiral slot 71 is formed and extends well beyond the finger flange to the plunger knob. This greatly facilitates molding of the barrel, including the spiral slot 71, without the use of any special technique. It will be appreciated that the position of the finger flange and the length of the barrel extension on the proximal side of the flange can be varied as required to retract needles of different lengths.

The distal end of the spiral slot 71 terminates within the thickness of the finger flange 17. Moreover, the radial length of the needle holder arm 32 is extended so that the end of the arm 32 projects beyond the outer surface of the barrel 70 and into a groove 72 formed in the flange 17, as a continuation of the distal end portion of the spiral channel 71 formed in the wall of the barrel. Consequently, when the arm 32 is positioned at the distal end of the spiral slot 71, the radially outer end portion of the arm 32 is positioned in the groove 72 formed in the flange 17.

This permits the use of a latch mechanism mounted on, or formed as a part of, the finger flange 17. A bead of resin may be glued to the end of the needle holder arm 32 projecting beyond the barrel wall to ensure that the arm remains engaged in the spiral slot 71.

In the particular embodiment illustrated in FIGS. 25 and 26, a latch 74 is molded as an integral part of the finger flange 17. The latch 74 includes an arm 75 connected to the flange 17 by a thin hinge 76 so that the arm 75 can be pivoted over the flange 17 to clamp the needle holder arm 32 against the flange 17. An L-shaped extension 77 on the free end of the arm 75 snaps over the flange 17 (see FIG. 26) to hold the arm 75 in its closed position until it is released by pressing on a rib 78 projecting from the opposite side of the arm 75. This is an advantageous construction in that it permits the latch to be molded as an integral part of the barrel 70.

An alternative latch construction for use with a circular finger flange is shown in FIGS. 27 and 28. In this embodiment, a separately molded, U-shaped latch element 80 fits over the portion of the flange 17 that contains the end portion of the needle holder arm 32. A series of detents 81 formed in the mating surfaces of the circular flange 17, a second flange 82 formed as an integral part of the barrel surface and the latch element 80 serve to hold the latch in position on the flange.

FIG. 29 illustrates a syringe similar to the syringe of FIG. 24 in that the spiral channel 60 extends through the wall of the barrel. In the design of FIG. 29, however, the spiral channel 60 is covered by separate sleeve 90 which is telescoped over, and attached to, the barrel 62. This sleeve 90 also forms the finger flange 17. This construction is particularly desirable when a portion of the spiral channel is located on the distal side of the finger flange 17, because that portion of the barrel is often gripped by the person using the syringe, and the smooth sleeve 90 has a better feel than a barrel surface having a spiral channel extending through the wall.

FIG. 30 is an end view of the proximal end of the barrel 62 and the sleeve 90 with the latch 63 removed. It can be seen that the slot 64 for the latch is formed in both the barrel 62 and the surrounding sleeve 90, and a hole 92 for the latching pin 67 is formed by the mating surfaces of the barrel 60 and the sleeve 90. Half of the hole 92 is formed in the inner surface of the sleeve 90, while the other half of the hole is formed in the outer surface of the barrel 62. When these two members are assembled, the mating surfaces form a circular hole 92 for receiving the latching pin 67.

Figure 32:
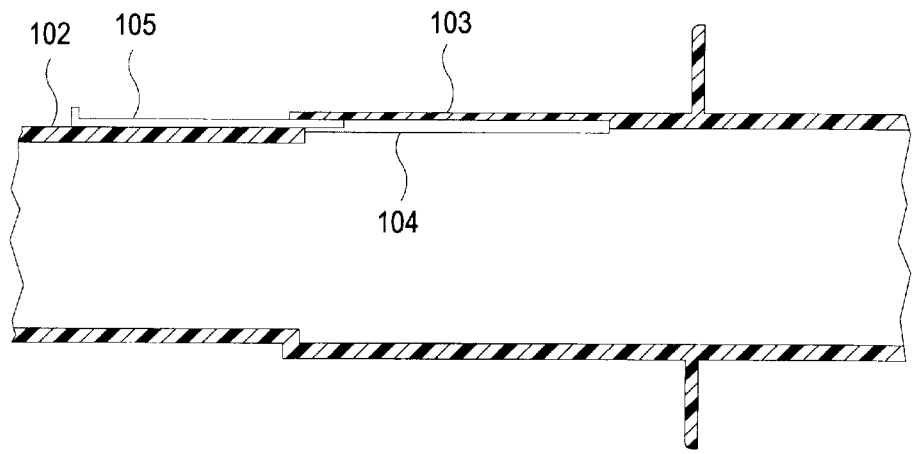

FIGS. 31–33 illustrate another modified barrel and latch. The barrel 100 in this embodiment is stepped at 101 so that both the inside diameter and the outside diameter of the barrel increase in the region containing the spiral channel, which is not shown in FIGS. 30–31. Because of the increase in the inside diameter of the barrel, the plunger will be supported only in the distal portion 102 of the barrel, while in the proximal portion 103 of the barrel a small gap will exist between the outer periphery of the plunger and the inner periphery of the barrel. The plunger will still be coaxially supported within the barrel because a substantial length of the plunger is always engaged within the distal portion 102 of the barrel. A channel 104 is formed in the inside surface of the proximal barrel portion 103 for receiving a latch 105. The sidewalls of the channel 104 guide and stabilize the latch 105 as it is moved back and forth between its advanced (closed) position within the spiral channel and its retracted (open) position outside the spiral channel.

I claim:

1. A needle-syringe assembly, comprising:
    an elongated, generally cylindrical barrel forming a hollow nozzle located at the distal end of said barrel and opening into the interior of said barrel;
    a plunger slidably mounted in said barrel and forming a longitudinal cavity;
    a needle holder slidably mounted in said longitudinal cavity of said plunger;
    guide means forming a spiral channel extending along a proximal end portion of said barrel for engaging a lateral extension of said needle holder and retracting said needle holder within the barrel in response to relative rotational movement between the barrel and the plunger, and
    latching means on said barrel for latching and unlatching said lateral extension of said needle holder at the distal end of said spiral channel.

2. The needle-syringe assembly of claim 1 wherein said latching means comprises a needle holder locking element slidably mounted on said barrel for reciprocating movement between a locking position within said spiral channel and a non-locking position outside said spiral channel.

3. The needle-syringe assembly of claim 2 wherein said latching means includes a manually actuatable handle attached to said needle holder locking element and exposed on the outer surface of said barrel for effecting sliding movement of said needle holder locking element.

4. The needle-syringe assembly of claim 2 wherein said latching means is slidably mounted in a channel formed in said barrel and opening into said spiral channel at one end of the channel, and opening through the end of said barrel at the other end of the channel.

5. The needle-syringe assembly of claim 1 wherein said plunger includes contacting means extending transversely across the interior of said barrel and sliding along the interior surface of said barrel that forms said spiral channel so as to maintain the desired configuration of that surface and thereby ensure engagement of said needle holder within said spiral channel.

6. The needle-syringe assembly of claim 5 wherein said contacting means includes a circular plate formed as an integral part of said plunger.

7. The needle-syringe assembly of claim 5 wherein said contacting means also includes a plurality of longitudinal elements formed as integral parts of said plunger and sliding along the interior surface of said barrel to maintain the desired configuration of that surface.

8. The needle-syringe assembly of claim 1 wherein said barrel includes an outwardly extending finger flange to facilitate gripping of the barrel, the distal end of said spiral channel terminates with said flange, and said needle holder extends radially through the barrel wall to said flange.

9. The needle-syringe assembly of claim 8 wherein said latching means is moveable over said flange to capture the portion of said needle holder that extends onto said flange.

10. The needle-syringe assembly of claim 1 wherein said spiral channel is formed in the wall of said barrel and extends radially through the wall of said barrel.

11. The needle-syringe assembly of claim 10 which includes an outer sleeve telescoped over said barrel and covering at least a distal end portion of said spiral channel.

12. The needle-syringe assembly of claim 1 wherein said latching means includes a longitudinal latching pin slidably mounted in the wall of said barrel for movement between a retracted (open) position outside said spiral channel and an advanced (closed) position in which the pin extends across said spiral channel to block the channel and capture said needle holder at the distal end of the channel.

13. The needle-syringe assembly of claim 12 wherein said spiral channel extends radially through the wall of said barrel and which includes a sleeve telescoped over said barrel and covering said spiral channel, the mating surfaces of said barrel and said sleeve forming a longitudinal passageway for receiving said latching pin.

14. The needle-syringe assembly of claim 1 wherein the portion of said barrel containing said spiral channel has a larger inside diameter than the distal portion of said barrel, and said latching means slides on the outer surface of said proximal portion of the barrel and on the inner surface of the barrel portion containing the spiral channel.

15. The needle-syringe assembly of claim 14 wherein the inner surface of the barrel portion containing the spiral channel forms a longitudinal channel for receiving and guiding said latching means.

16. The needle-syringe assembly of claim 1 wherein said lateral extension comprises a lateral arm extending laterally through said plunger cavity to said barrel, and said latching means is mounted for movement out of said spiral channel for capturing and releasing said needle holder arm at the distal end of said spiral channel.

17. The needle-syringe assembly of claim 1 which includes a hollow needle attached to the distal end of said needle holder.

18. The needle-syringe assembly of claim 1 wherein said spiral channel includes means at the proximal end thereof for resisting advancing movement of said needle holder after it has been fully retracted.

19. The needle-syringe assembly of claim 1 which includes a detent at the distal end of said spiral channel.

20. The needle-syringe assembly of claim 1 wherein said latching means includes a slidable plate which forms a distal end portion of a side wall of said spiral, channel when said plate is in a retracted (open) position, and which blocks said channel and captures said needle holder at the distal end of said channel when said plate is in an advanced (closed) position.

21. The needle syringe assembly of claim 1 wherein said cavity of said plunger forms locking fingers, said locking fingers securing said arm of said needle holder in place.

* * * * *